(12) United States Patent
Mou et al.

(10) Patent No.: US 11,304,632 B2
(45) Date of Patent: Apr. 19, 2022

(54) BLOOD GLUCOSE DETECTION DEVICE

(71) Applicant: Microjet Technology Co., Ltd., Hsinchu (TW)

(72) Inventors: Hao-Jan Mou, Hsinchu (TW); Li-Pang Mo, Hsinchu (TW); Chi-Feng Huang, Hsinchu (TW); Yung-Lung Han, Hsinchu (TW); Wei-Ming Lee, Hsinchu (TW); Hsuan-Kai Chen, Hsinchu (TW)

(73) Assignee: MICROJET TECHNOLOGY CO., LTD., Hsinchu (TW)

( * ) Notice: Subject to any disclaimer, the term of this patent is extended or adjusted under 35 U.S.C. 154(b) by 316 days.

(21) Appl. No.: 16/170,632

(22) Filed: Oct. 25, 2018

(65) Prior Publication Data
US 2019/0150806 A1    May 23, 2019

(30) Foreign Application Priority Data
Nov. 20, 2017    (TW) ................. 106140073

(51) Int. Cl.
A61B 5/145    (2006.01)
A61B 5/15     (2006.01)
(Continued)

(52) U.S. Cl.
CPC ...... *A61B 5/14514* (2013.01); *A61B 5/14532* (2013.01); *A61B 5/157* (2013.01);
(Continued)

(58) Field of Classification Search
CPC ............ A61B 5/14514; A61B 5/14532; A61B 5/150099; A61B 5/14503;
(Continued)

(56) References Cited

U.S. PATENT DOCUMENTS 6,558,361 B1 * 5/2003 Yeshurun .......... A61M 37/0015
                                                 604/272
7,344,499 B1 * 3/2008 Prausnitz ......... A61M 37/0015
                                                 600/309
(Continued)

FOREIGN PATENT DOCUMENTS

CN        1916639 A1    2/2007
CN      101377192 A     3/2009
(Continued)

OTHER PUBLICATIONS

Saggere, "Membrane Actuation for Micropumps", 2008, In: Li D. (Eds.), Encyclopedia of Microfluidics and Nanofluidics (pp. 1078-1082). Boston, MA: Springer. (Year: 2008).*
(Continued)

*Primary Examiner* — Eric J Messersmith
(74) *Attorney, Agent, or Firm* — Birch, Stewart, Kolasch & Birch, LLP

(57) ABSTRACT

A blood glucose detection device includes a carrier body, a flow-guiding actuator, a microneedle patch, a sensor and a controlling chip. The carrier body has a liquid guiding channel, a compressing chamber and a liquid storage chamber. The flow-guiding actuator seals the compressing chamber. The microneedle patch is attached on the carrier body and has plural hollow microneedles. The sensor is disposed within the liquid storage chamber. The controlling chip is disposed on the carrier body. The plural hollow microneedles puncture the skin of a human subject with minimal invasion. The controlling chip controls the flow-guiding actuator to actuate and the tissue fluid is sucked into the liquid storage chamber through the plural hollow microneedles, whereby the sensor detects the blood glucose of the tissue fluid to generate and transmit the measured data
(Continued)

to the controlling chip. The controlling chip can generate monitoring information by calculating the measured data.

14 Claims, 6 Drawing Sheets

(51) Int. Cl.
    *A61B 5/157*     (2006.01)
    *A61B 5/00*     (2006.01)
    *A61B 10/00*     (2006.01)

(52) U.S. Cl.
    CPC .. *A61B 5/150022* (2013.01); *A61B 5/150083* (2013.01); *A61B 5/15087* (2013.01); *A61B 5/150099* (2013.01); *A61B 5/150221* (2013.01); *A61B 5/150854* (2013.01); *A61B 5/150862* (2013.01); *A61B 5/150969* (2013.01); *A61B 5/150984* (2013.01); *A61B 5/4839* (2013.01); *A61B 5/685* (2013.01); *A61B 10/0045* (2013.01); *A61B 5/0002* (2013.01); *A61B 2010/008* (2013.01); *A61B 2562/166* (2013.01); *A61B 2562/227* (2013.01)

(58) Field of Classification Search
    CPC ........ A61B 5/150022; A61B 5/150221; A61B 5/150854; A61B 5/150862; A61B 5/15087; A61B 5/150969; A61B 5/150977; A61B 5/6833; A61B 5/157; A61B 5/4839; A61B 5/685; A61B 5/14546; A61B 5/1459; A61B 5/150282; A61B 5/150229; A61B 5/150984; A61B 10/0045; A61B 5/145; A61B 10/00; A61B 5/00; A61B 5/15; A61B 5/150083; A61B 2010/008; A61B 2562/166; A61B 2562/227; A61B 5/0002; B81B 2201/055; B81B 2201/05; G05D 7/0694; F16K 99/0026; F16K 2099/0084
See application file for complete search history.

(56) References Cited

U.S. PATENT DOCUMENTS

| | | | |
|---|---|---|---|
| 8,160,665 B2 | 4/2012 | Mischler et al. | |
| 2003/0187423 A1 | 10/2003 | Wilkinson et al. | |
| 2003/0191376 A1* | 10/2003 | Samuels | A61B 5/157 600/309 |
| 2005/0228313 A1* | 10/2005 | Kaier | A61B 5/14532 600/583 |
| 2005/0266571 A1* | 12/2005 | Stout | A61B 5/14514 436/55 |
| 2009/0060750 A1* | 3/2009 | Chen | F04B 43/043 417/26 |
| 2009/0131778 A1 | 5/2009 | Jina et al. | |
| 2013/0079666 A1* | 3/2013 | Gonzalez-Zugasti | A61B 5/15113 600/583 |
| 2016/0066894 A1* | 3/2016 | Barton-Sweeney | A61B 10/0012 600/301 |
| 2016/0242689 A1* | 8/2016 | Roehr | A61B 5/150389 |

FOREIGN PATENT DOCUMENTS

| | | | |
|---|---|---|---|
| EP | 1590034 B1 | 5/2014 | |
| WO | WO 2006/105146 A2 | 10/2006 | |
| WO | WO-2011053788 A2 * | 5/2011 | ............ A61B 5/685 |
| WO | WO 2013/132206 A1 | 9/2013 | |
| WO | WO 2014/160804 A2 | 10/2014 | |

OTHER PUBLICATIONS

Extended European Search Report for European Application No. 18202499.2, dated Feb. 18, 2019.
Indian Office Action for Application No. 201824040265, dated Mar. 12, 2021.

* cited by examiner

BLOOD GLUCOSE DETECTION DEVICE

FIELD OF THE INVENTION

The present disclosure relates to a blood glucose detection device, and more particularly to a blood glucose detection device for human blood glucose detection.

BACKGROUND OF THE INVENTION

For diabetes mellitus patients, self-detection of blood glucose plays an important role in the management of blood glucose. Currently, the blood glucose meter used to measure blood glucose is inconvenient to carry, so it is difficult for patients to monitor the blood glucose level when they go out. In addition, in the process of measuring blood glucose, sometimes the patient's skin has been punctured with a needle but there is little or even without bleeding. Under this situation, it is necessary to re-needle or force to squeeze the blood out. This may cause the psychological fear of the patient, and which is necessary to be improved.

Therefore, there is a need of providing a blood glucose detection device to address the above-mentioned issues as using the conventional blood glucose measuring method. The blood glucose detection device should be intelligent, safe, portable and painless, allowing the patients to measure the blood glucose level in daily life so as to control the level of the blood glucose anytime.

SUMMARY OF THE INVENTION

The conventional blood glucose measuring method causes the patients' pain and the blood glucose meter is inconvenient to carry. The object of the present disclosure is to provide a blood glucose detection device to overcome the problems in the current situation. In accordance with an aspect of the present disclosure, a blood glucose detection device is provided. The blood glucose detection device includes a carrier body, a flow-guiding actuator, a microneedle patch, a sensor and a controlling chip. The carrier body has a liquid guiding channel, a compressing chamber and a liquid storage chamber. The liquid guiding channel includes an inlet channel and a liquid storage channel separately disposed on the carrier body. The compressing chamber is in fluid communication with the inlet channel and the liquid storage channel, and the liquid storage channel is in fluid communication with the liquid storage chamber. The flow-guiding actuator is constructed on the carrier body and seals the compressing chamber. The microneedle patch is attached on the carrier body and is in fluid communication with the inlet channel. The microneedle patch has plural hollow microneedles adapted to puncture the skin of a human subject with minimal invasion so as to suck the tissue fluid therein. The sensor is systematic packaged on the carrier body and is disposed within the liquid storage chamber. The sensor is used to measure the blood glucose of the tissue fluid and generate measured data correspondingly, thereby monitoring the blood glucose level of the human subject. The controlling chip is systematic packaged on the carrier body. The controlling chip controls the actuation of the flow-guiding actuator, and receives the measured data from the sensor. In this way, after the plural hollow microneedles of the microneedle patch punctures the skin of the human subject with minimal invasion, the controlling chip controls the flow-guiding actuator to actuate and a pressure difference is generated in the compressing chamber. Then, the tissue fluid is sucked into the inlet channel through the plural hollow microneedles and transported to the liquid storage chamber, whereby the sensor detects the blood glucose of the tissue fluid and transmits the measured data to the controlling chip for calculation. The controlling chip can generate monitoring information by calculating the measured data and provide the human subject with the monitoring information for reference.

The above contents of the present disclosure will become more readily apparent to those ordinarily skilled in the art after reviewing the following detailed description and accompanying drawings, in which:

DETAILED DESCRIPTION OF THE PREFERRED EMBODIMENT

The present disclosure will now be described more specifically with reference to the following embodiments. It is to be noted that the following descriptions of preferred embodiments of this disclosure are presented herein for purpose of illustration and description only. It is not intended to be exhaustive or to be limited to the precise form disclosed.

Figure 1:
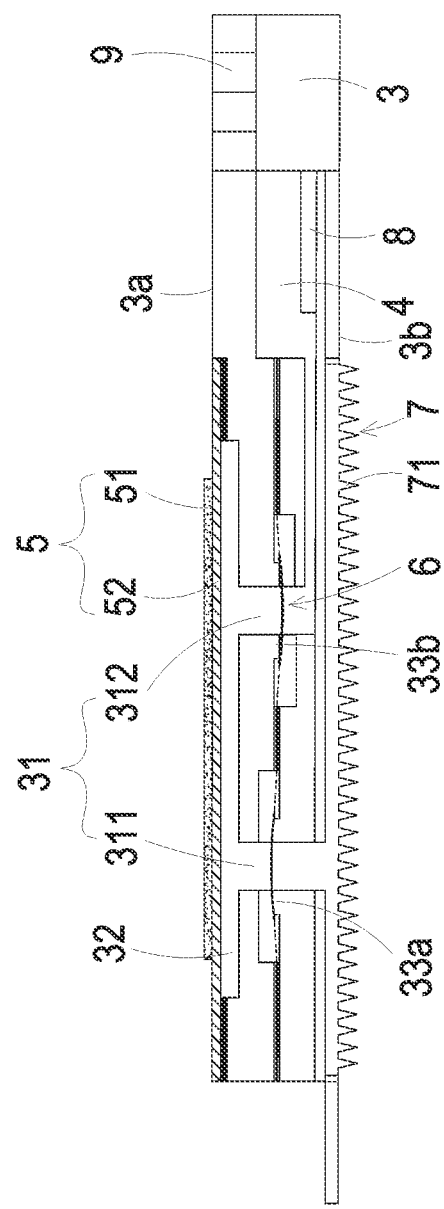
FIG. 1 is a schematic structural view illustrating a blood glucose detection device according to an embodiment of the present disclosure.

FIG. 1 is a schematic structural view illustrating a blood glucose detection device according to an embodiment of the present disclosure. Referring to FIG. 1. The present discourse provides a blood glucose detection device 100, wherein the blood glucose detection device 100 includes at least one carrier body 3, at least one liquid guiding channel 31, at least one compressing chamber 32, at least one liquid storage chamber 4, at least one inlet channel 311, at least one liquid storage channel 312, at least one flow-guiding actuator 5, at least one microneedle patch 7, at least one tissue fluid, at least one sensor 8, at least one measured data, at least one controlling chip 9, at least one pressure difference and at least one monitoring information. The number of the carrier body 3, the liquid guiding channel 31, the compressing chamber 32, the liquid storage chamber 4, the inlet channel 311, the liquid storage channel 312, the flow-guiding actuator 5, the microneedle patch 7, the tissue fluid, the sensor 8, the measured data, the controlling chip 9, the pressure difference and the monitoring information is exemplified by one for each in the following embodiments but not limited thereto. It is noted that each of the carrier body 3, the liquid guiding channel 31, the compressing chamber 32, the liquid storage chamber 4, the inlet channel 311, the liquid storage channel 312, the flow-guiding actuator 5, the microneedle patch 7, the tissue fluid, the sensor 8, the measured data, the controlling chip 9, the pressure difference and the monitoring information can also be provided in plural numbers.

The present disclosure discloses a blood glucose detection device 100. Please refer to FIG. 1. The blood glucose detection device 100 includes a carrier body 3, a liquid storage chamber 4, a flow-guiding actuator 5, a microneedle patch 7, a sensor 8 and a controlling chip 9. The carrier body 3 has a liquid guiding channel 31 and a compressing chamber 32. The liquid guiding channel 31 further includes an inlet channel 311 and a liquid storage channel 312, which are separately disposed on the carrier body 3. The compressing chamber 32 is in fluid communication with the inlet channel 311 and the liquid storage channel 312, and the liquid storage channel 312 is in fluid communication with the liquid storage chamber 4. The liquid storage chamber 4 is concavely formed on the carrier body 3 and used to store the tissue fluid. The flow-guiding actuator 5 is constructed on a first surface 3a of the carrier body 3 and seals the compressing chamber 32. After the flow-guiding actuator 5 is actuated, a suction force is generated so as to suck the tissue fluid. The microneedle patch 7 is mounted on a second surface 3b opposite to the first surface 3a of the carrier body 3 and is in fluid communication with the inlet channel 311. The microneedle patch 7 has plural hollow microneedles 71 that may be used to puncture the skin of a human subject with minimal invasion. In some embodiment, the microneedle patch 7 having the plural hollow microneedles 71 may be combined with other noninvasive ways in practice. Moreover, the sensor 8 and the driving chip 9 are integrated via microelectronmechanical systems (MEMS) procedure and mounted on the carrier body 3. The sensor 8 is systematic packaged on the carrier body 3 and is disposed within the liquid storage chamber 4. The controlling chip 9 is also systematic packaged on the carrier body 3 for controlling the actuation of the flow-guiding actuator 5 and receiving and analyzing the measured data from the sensor 8.

Figure 2:
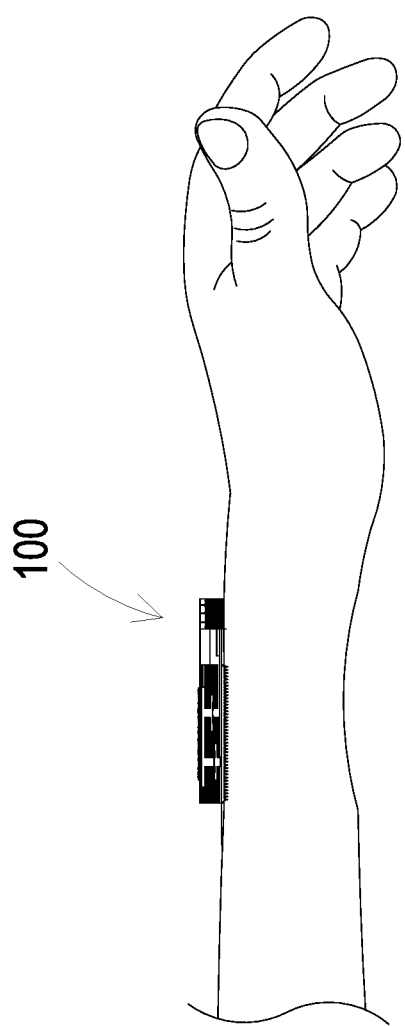
FIG. 2 is a schematic structural view illustrating the blood glucose detection device to be used on user's body.

FIG. 2 is a schematic structural view illustrating the blood glucose detection device to be used on user's body. Referring to FIGS. 1 and 2. In some embodiments, after the plural hollow microneedles 71 of the microneedle patch 7 puncture the skin of the human subject, the controlling chip 9 drives the flow-guiding actuator 5 to vibrate vertically to expand or compress the volume of the compressing chamber 32, so that the pressure in the interior of the compressing chamber 32 is changed and a suction force is generated accordingly. The suction force in the inlet channel 311 allows the plural hollow microneedles 71 to suck the tissue fluid from the human subject. The tissue fluid flows through the compressing chamber 32 and the liquid storage channel 312 into the interior of liquid storage chamber 4. In the mean time, the sensor 8 detects the composition of the tissue fluid and measures the blood glucose level of it. Subsequently, the sensor 8 generates the measured data relating to the blood glucose level and then transmits the same to the controlling chip 9 for calculation. The controlling chip 9 can generate the monitoring information by calculating the measured data and provide the user (e.g., the human subject) with the monitoring information for reference. In another embodiment, the tissue fluid is a human subcutaneous tissue fluid.

The hollow microneedles 71 of the microneedle patch 7 are micron-sized needles capable of puncturing the patient's skin. The hollow microneedles 71 may be made of high molecular polymer, metal or silicon. Preferably but not exclusively, the hollow microneedles 71 are made of silicon dioxide with high biocompatibility. The size of the hollow part inside each hollow microneedle 71 is suitable for allowing the human subcutaneous tissue fluid to pass through. Preferably, the microneedle 71 has an internal diameter ranging from 10 μm to 550 μm. The microneedle 71 has a length ranging from 400 μm to 900 μm. The hollow microneedles 71 can puncture into the human subject's subcutaneous tissue to reach a depth and without contacting any nerve. Therefore, the puncture of the hollow microneedles 71 is painless. The hollow microneedles 71 are disposed on the microneedle patch 7 and arranged in an array. The hollow microneedles 71 are spaced from each other a distance greater than 200 μm, by which the hollow microneedles 71 would not interfere with each other regarding the liquid transportation. When blockage of one or more hollow microneedles 71 occurs, the rest of the hollow microneedles 71 without blockage can still function. That is, the arrangement of the hollow microneedles 71 in the array can prevent the entire liquid flowing function from being impacted.

Figure 3:
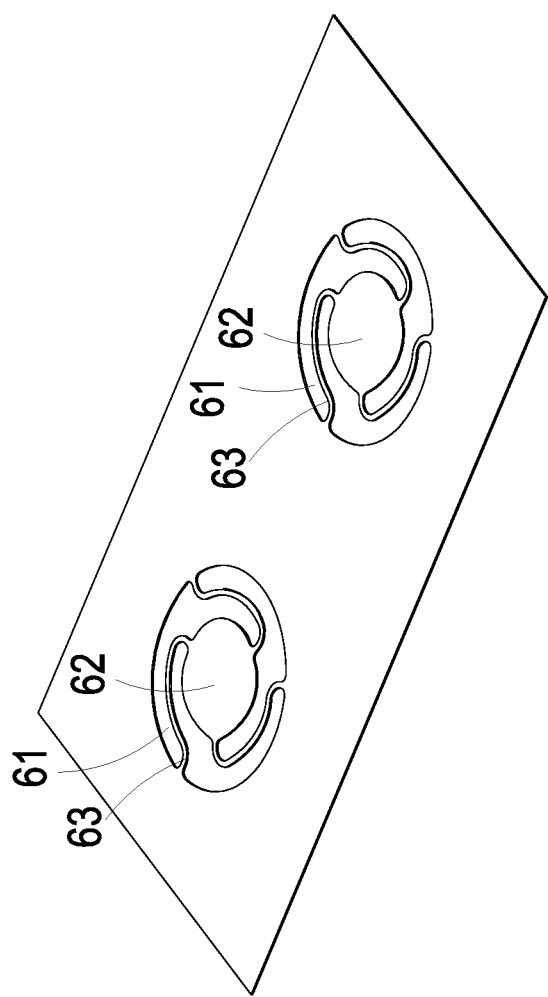
FIG. 3 is a schematic structural view illustrating the valve membrane of the blood glucose detection device according to the present disclosure.

FIG. 3 is a schematic structural view illustrating the valve membrane of the blood glucose detection device according to the present disclosure. Please refer to FIGS. 1 to 3. In this blood glucose detection device 100, a valve membrane 6 is disposed in the inlet channel 311 and the liquid storage channel 312. A plurality of through holes 61 are formed on the valve membrane 6. There are convex structures 33a, 33b respectively formed in the inlet channel 311 and the liquid storage channel 312 of the carrier body 3, wherein the protruding direction of the convex structure 33a of the inlet channel 311 is opposite to the protruding direction of the convex structure 33b of the liquid storage channel 312. In this embodiment, the protruding direction of the convex structure 33a of the inlet channel 311 is upward, but on the contrary, the protruding direction of the convex structure 33a of the inlet channel 311 is downward. The valve membrane 6 has plural through holes 61 spatially corresponding to the partial area of the compressing chamber 32 and has a central part 62 connected to plural connection parts 63. The central part 62 can be elastically supported by the connection parts 63 that divide the space between the central part 62 and the connection parts 63 into the plural through holes 61. Consequently, the convex structures 33a, 33b abut against the valve membrane 6 and seal the plural through holes 61, respectively, and a pre-force is formed. The pre-force brings the valve membrane 6 into close contact with the convex structures 33a, 33b. In the above-mentioned configuration, when the flow-guiding actuator 5 is non-enabled, the central parts 62 of the valve membrane 6 in the inlet channel 311 and the liquid storage channel 312 can close the inlet channel 311 and the liquid storage channel 312, respectively. Therefore, the tissue fluid transported between the inlet channel 311 and the liquid storage channel 312 will not be reversely returned. That is, the tissue fluid flows in a single direction from the inlet channel 311 to the liquid storage channel 312 without flowing back.

In some embodiments, the flow-guiding actuator 5 includes an actuating element 51 and a carrying member 52. The carrying member 52 covers and seals the compressing chamber 32, and the actuating element 51 is attached on a surface of the carrying member 52. The actuating element 51 is subject to a deformation to drive the carrying member 52 to vibrate up and down. Consequently, the volume of the compressing chamber 32 is varied to change the pressure in the interior of the compressing chamber 32 so as to generate a suction force to transport the tissue fluid. In another embodiment, the actuating element 51 is a piezoelectric component.

Figure 4A:
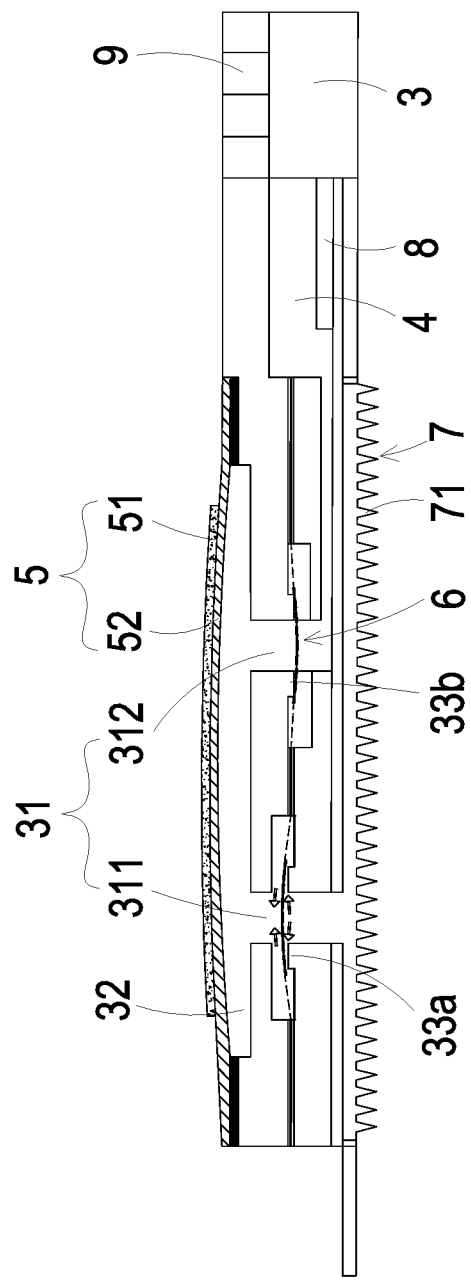
FIGS. 4A and 4B show the actuations of the blood glucose detection device of FIG. 1.
Figure 4B:
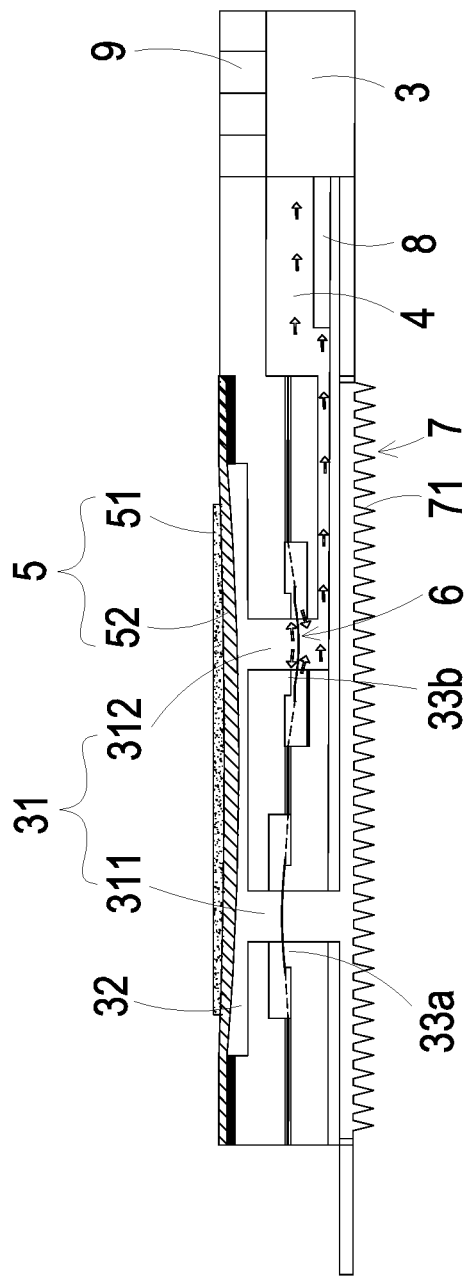

FIGS. 4A and 4B show the actuations of the blood glucose detection device of FIG. 1. Referring to FIGS. 4A and 4B, when the flow-guiding actuator 5 receives a driving signal from the controlling chip 9, the actuating element 51 is subject to the deformation due to the piezoelectric effect so as to drive the carrying member 52 attached on the actuating element 51 to vibrate up and down. Referring to FIG. 4A, when the carrying member 52 moves upwardly in response to the actuating element 51, the volume of the compressing chamber 32 is increased and a negative pressure is generated. The negative pressure drives the valve membrane 6 in the inlet channel 311 to move upwardly that the central part 62 (as shown in FIG. 3) of the valve membrane 6 moves away from the convex structure 33a. Because of the negative pressure of the compressing chamber 32 being in fluid communication with the inlet channel 311, the tissue fluid is sucked via the microneedle patch 7 and then flows through the inlet channel 311 and the at least one through hole 61 (as shown in FIG. 3) of the valve membrane 6 into the compressing chamber 32. Referring to FIG. 4B, since the controlling chip 9 continuously outputs the driving signal to the flow-guiding actuator 5, the actuating element 51 then drives the carrying member 52 to move downwardly. The volume of the compressing chamber 32 is compressed to generate a pushing force that drives the valve membrane 6 in liquid storage channel 312 to move downwardly. That is, the central part 62 (as shown in FIG. 3) of the valve membrane 6 also moves away from the convex structure 33b. The tissue fluid within the compressing chamber 32 is pushed into the liquid storage channel 312 and flows through the at least one through hole 61 (as shown in FIG. 3) into the liquid storage chamber 4.

Figure 5:
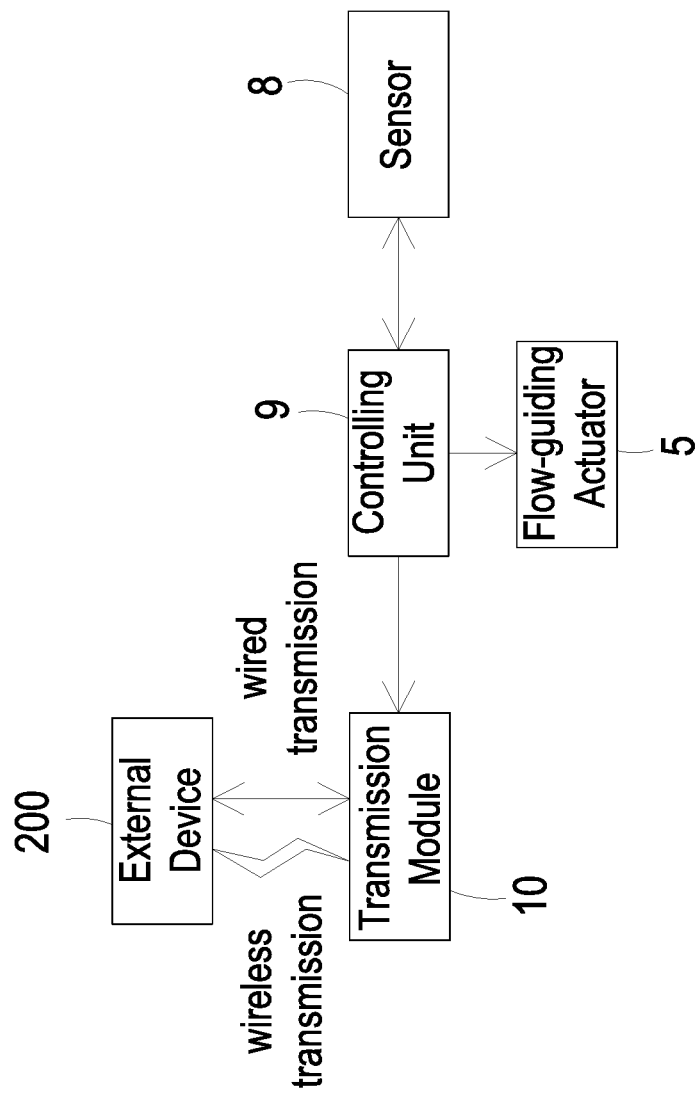
FIG. 5 is a block diagram of the blood glucose detection device according to the embodiment of the present disclosure.

Please refer to FIGS. 1 and 5. FIG. 5 is a block diagram of the blood glucose detection device according to the embodiment of the present disclosure. In this embodiment, the blood glucose detection device 100 further includes a transmission module 10. The controlling chip 9 constructed on the carrier body 3 is electrically connected to the flow-guiding actuator 5, the sensor 8 and the transmission module 10. The sensor 8 is used to detect the blood glucose of the human subcutaneous tissue fluid and generate measured data regarding the blood glucose level correspondingly. Then, the sensor 8 transmits the measured data to the controlling chip 9 for analysis. After the controlling chip 9 receives the measured data from the sensor 8, the controlling chip 9 generates monitoring information by analyzing the measured data and then transmits the monitoring information to the transmission module 10. The monitoring information could be transmitted to an external device 200 through the transmission module 10. In some embodiments, the external device 200 may be at least one selected from the group consisting of a cloud system, a portable device, a computer system, a monitor, an insulin injection device and so on. In some embodiments, the controlling chip 9 includes a graphene battery (not shown) for power supply.

Furthermore, the transmission module 10 may transmit the information to the external device 200 via a wired transmission technology or a wireless transmission technology. The wired transmission technology includes a wired transmission module. The wired transmission module may be at least one selected from the group consisting of a USB port, a mini-USB port and a micro-USB port. The wireless transmission technology includes a wireless transmission module. The wireless transmission module may be at least one selected from the group consisting of a Wifi module, a Bluetooth module, an RF module and a NFC module.

From the above descriptions, the present disclosure provides a blood glucose detection device. After the plural hollow microneedles of the microneedle patch are punctured into the human subcutaneous tissue, the flow-guiding actuator is enabled to generate a pressure gradient in the compressing chamber. The pressure gradient creates a suction force that makes the plural hollow microneedles suck the tissue liquid into it. The tissue liquid flows through the liquid guiding channel into the liquid storage chamber and is detected by the sensor disposed therein. The sensor within the liquid storage chamber measures the blood glucose level of the tissue fluid and generates the measured data correspondingly. The controlling chip generates monitoring information by analyzing the measured data and transmits the monitoring information to the transmission module. At last, the user may be provided with the monitoring information for reference. Moreover, the installation of the graphene battery allows the present disclosure to be unplugged, so the blood glucose measurement could be easy, simple and conducted at any time and any place. It reduces the inconvenience of measuring the level of the blood glucose by the user. In addition, for monitoring the blood glucose level, the non-invasive or minimal invasive method can be implemented by utilizing the microneedle patch of the present disclosure. Obtaining the tissue fluid by the non-invasive or minimal invasive method can reduce the burden of the user, avoid the generation of wounds and reduce the risk of infection.

While the disclosure has been described in terms of what is presently considered to be the most practical and preferred embodiments, it is to be understood that the disclosure needs not be limited to the disclosed embodiments. On the contrary, it is intended to cover various modifications and similar arrangements included within the spirit and scope of the appended claims which are to be accorded with the broadest interpretation so as to encompass all such modifications and similar structures.

What is claimed is:
1. A blood glucose detection device, comprising:
  a carrier body having a liquid guiding channel, a compressing chamber and a liquid storage chamber, wherein the liquid guiding channel includes an inlet channel and a liquid storage channel separately disposed on the carrier body, the compressing chamber is in fluid communication with the inlet channel and the liquid storage channel, and the liquid storage channel is in fluid communication with the liquid storage chamber;
  a flow-guiding actuator constructed on a first surface of the carrier body and comprising a carrying member and an actuating element, wherein the carrying member covers and sealing the compressing chamber, and the actuating element is attached to a surface of the carrying member, wherein the actuating element is supplied with power and is subject to deformation to drive the carrying member to vibrate up and down so as to compress the volume of the compressing chamber to generate a suction force, and a tissue fluid is transported to the liquid storage chamber;
  a microneedle patch mounted on a second surface opposite to the first surface of the carrier body and being in fluid communication with the inlet channel, wherein the microneedle patch has plural hollow microneedles adapted to puncture skin of a human subject with minimal invasion so as to suck the tissue fluid of the human subject; a sensor systematic packaged on the carrier body and disposed within the liquid storage chamber, wherein the sensor measures a blood glucose level of the tissue fluid and generates measured data correspondingly; and a controlling chip systematic packaged on the first surface of the carrier body and disposed in one side of the flow-guiding actuator, wherein the flow-guiding actuator, the microneedle patch, the sensor, the controlling chip are all compactly arranged on the carrier body in both a vertical phase and a horizontal phase, and the liquid storage chamber is disposed adjacent the microneedle patch and arranged between the flow-guiding actuator and the controlling chip, and the sensor and the controlling chip are integrated via microelectronmechanical systems procedure and mounted on the carrier body, and the controlling chip is configured to control the flow-guiding actuator to actuate to generate a pressure difference in the compressing chamber after the plural hollow microneedles of the microneedle patch puncture the skin of the human subject, so that the tissue fluid is sucked into the inlet channel through the plural hollow microneedles and transported to the liquid storage chamber, whereby the sensor detects the blood glucose of the tissue fluid stored in the liquid storage chamber and transmits the measured data to the controlling chip for calculation, and the controlling chip is configured to generate and provide the human subject with monitoring information by calculating the measured data.

2. The blood glucose detection device according to claim 1, wherein the tissue fluid is a human subcutaneous tissue fluid.

3. The blood glucose detection device according to claim 1, wherein the actuating element is a piezoelectric component.

4. The blood glucose detection device according to claim 1, wherein a valve membrane is disposed in the inlet channel and the liquid storage channel, wherein the valve membrane closes and seals the inlet channel and the liquid storage channel, thereby controlling open/closed states of the inlet channel and the liquid storage channel.

5. The blood glucose detection device according to claim 4, wherein the carrier body further comprises a convex structure in each of the inlet channel and the liquid storage channel, and the convex structure is configured to provide a pre-force when the valve membrane is abutting against the convex structure, thereby preventing the tissue fluid from flowing back.

6. The blood glucose detection device according to claim 1, wherein the controlling chip comprises a graphene battery for providing power.

7. The blood glucose detection device according to claim 1, wherein the controlling chip comprises a transmission module for transmitting the monitoring information to an external device.

8. The blood glucose detection device according to claim 7, wherein the transmission module is a wired transmission module, wherein the wired transmission module is at least one selected from the group consisting of a USB port, a mini-USB port and a micro-USB port.

9. The blood glucose detection device according to claim 8, wherein the transmission module is a wireless transmission module, wherein the wireless transmission module is at least one selected from the group consisting of a Wifi module, an RF module and a NFC module.

10. The blood glucose detection device according to claim 7, wherein the external device is at least one selected from the group consisting of a cloud system, a portable device, a computer system, a monitor and an insulin injection device.

11. The blood glucose detection device according to claim 1, wherein each of the plural hollow microneedles of the microneedle patch has an internal diameter ranging from 10 µm to 550 µm and a length ranging from 400 µm to 900 µm.

12. The blood glucose detection device according claim 1, wherein the plural hollow microneedles are arranged in an array, and the plural hollow microneedles are spaced from each other a distance greater than 200 µm.

13. The blood glucose detection device according claim 1, wherein the plural hollow microneedles are made of silicon dioxide.

14. A blood glucose detection device, comprising:
at least one carrier body having at least one liquid guiding channel, at least one compressing chamber and at least one liquid storage chamber, wherein the at least one liquid guiding channel includes at least one inlet channel and at least one liquid storage channel separately disposed on the at least one carrier body, the at least one compressing chamber is in fluid communication with the at least one inlet channel and the at least one liquid storage channel, and the at least one liquid storage channel is in fluid communication with the at least one liquid storage chamber;

at least one flow-guiding actuator constructed on at least one first surface of the at least one carrier body and comprising at least one carrying member and at least one actuating element, wherein the at least one carrying member covers and sealing the at least one compressing chamber, and the at least one actuating element is attached to at least one surface of the at least one carrying member, wherein the at least one actuating element is supplied with power and is subject to deformation to drive the at least one carrying member to vibrate up and down so as to compress the volume of the at least one compressing chamber to generate at least one suction force, and at least one tissue fluid is transported to the at least one liquid storage chamber;

at least one microneedle patch mounted on at least one second surface opposite to the at least one first surface of the at least one carrier body and being in fluid communication with the at least one inlet channel, wherein the at least one microneedle patch has plural hollow microneedles adapted to puncture skin of a human subject with minimal invasion so as to suck the at least one tissue fluid of the human subject;

at least one sensor systematic packaged on the at least one carrier body and disposed within the at least one liquid storage chamber, wherein the at least one sensor measures the blood glucose level of the at least one tissue fluid and generates at least one measured data correspondingly; and at least one controlling chip systematic packaged on the at least one first surface of the at least one carrier body the carrier body and disposed in one side of the at least one flow-guiding actuator;

wherein the at least one flow-guiding actuator, the at least one microneedle patch, the at least one sensor, the at least one controlling chip are all compactly arranged on the at least one carrier body in both a vertical phase and a horizontal phase, and the at least one liquid storage chamber is disposed adjacent the at least one microneedle patch and arranged between the at least one flow-guiding actuator and the at least one controlling chip, and the at least one sensor and the at least one controlling chip are integrated via microelectronmechanical systems procedure and mounted on the at least one carrier body, and the at least one controlling chip is configured to control the at least one flow-guiding actuator to actuate to generate at least one pressure difference in the at least one compressing chamber after the plural hollow microneedles of the at least one microneedle patch puncture the skin of the human subject, so that the at least one tissue fluid is sucked into the at least one inlet channel through the plural hollow microneedles and transported to the at least one liquid storage chamber, whereby the at least one sensor detects the blood glucose of the at least one tissue fluid stored in the at least one liquid storage chamber and transmits the at least one measured data to the at least one controlling chip for calculation, and the at least one controlling chip is configured to generate and provide the human subject with monitoring information by calculating the at least one measured data.

* * * * *